United States Patent [19]

Ghosh et al.

[11] Patent Number: 5,847,255
[45] Date of Patent: Dec. 8, 1998

[54] GAS PHASE ALKYLATION-LIQUID PHASE TRANSALKYLATION PROCESS

[75] Inventors: Ashim Kumar Ghosh, Houston; James T. Merrill, Katy; James R. Butler, Houston, all of Tex.

[73] Assignee: Fina Technology, Inc., Dallas, Tex.

[21] Appl. No.: 861,206

[22] Filed: May 21, 1997

[51] Int. Cl.⁶ .................................................. G07C 2/66
[52] U.S. Cl. ........................ 585/467; 585/303; 585/323; 585/447; 585/449; 585/467; 585/475
[58] Field of Search .................................... 585/303, 323, 585/447, 449, 467, 475

[56] References Cited

U.S. PATENT DOCUMENTS

| | | | |
|---|---|---|---|
| 4,107,224 | 8/1978 | Dwyer | 260/671 R |
| 4,169,111 | 9/1979 | Wight | 585/323 |
| 4,185,040 | 1/1980 | Ward et al. | 585/467 |
| 4,489,214 | 12/1984 | Butler et al. | 585/467 |
| 4,520,220 | 5/1985 | Watson et al. | 585/467 |
| 4,599,473 | 7/1986 | Debras et al. | 585/467 |
| 4,774,379 | 9/1988 | Butler et al. | 585/467 |
| 4,781,906 | 11/1988 | Cahen et al. | 423/328 |
| 4,922,053 | 5/1990 | Waguespack et al. | 585/449 |

FOREIGN PATENT DOCUMENTS

467007 A1   1/1992   European Pat. Off. .

*Primary Examiner*—Glenn Caldarola
*Assistant Examiner*—Thuan D. Dang
*Attorney, Agent, or Firm*—Pamela S. Smith; William D. Jackson; M. Norwood Cheairs

[57] ABSTRACT

Process for the production of ethylbenzene by alkylation over a silicalite alkylation catalyst with the subsequent transalkylation of diethylbenzene with the alkylation catalyst and conditions selected to retard xylene production and also heavies production. A feedstock containing benzene and ethylene is applied to a multi-stage alkylation reaction zone having a plurality of series-connected catalyst beds containing a pentasil molecular sieve alkylation catalyst which is silicalite of a predominantly monoclinic symmetry having a silica/alumina ratio of at least 275. The feedstock is supplied to the alkylation reaction zone to cause gas-phase ethylation of benzene at a flow rate to provide a space velocity of benzene over the catalyst to produce a xylene concentration in the product of about 600 ppm or less based upon the ethylbenzene content. Periodically the space velocity may be increased to a value which is greater than the space velocity associated with a minimum concentration of diethylbenzene in the alkylation product such that diethylbenzene production is enhanced while minimizing any attendant transalkylation reactions within the alkylation reaction zone. This is accompanied by a relatively low xylene content in the product, specifically no more than 600 ppm based upon the ethylbenzene in the product. The output from the alkylation reactor is applied to an intermediate recovery zone for the separation and recovery of ethylbenzene with the recovery of a polyalkylated aromatic component which is supplied along with benzene to a transalkylation reaction zone where the polyalkylated aromatic fraction is subject to disproportionation to provide a reduced diethylbenzene content and an enhanced ethylbenzene content.

21 Claims, 5 Drawing Sheets

5,847,255

GAS PHASE ALKYLATION-LIQUID PHASE TRANSALKYLATION PROCESS

FIELD OF THE INVENTION

This invention involves an aromatic alkylation/transalkylation process involving vapor phase ethylation of benzene over a silicalite aromatic alkylation catalyst under conditions providing enhanced diethylbenzene production and diminished xylene production and followed by a subsequent liquid phase transalkylation over a relatively large pore size zeolite transalkylation catalyst.

BACKGROUND OF THE INVENTION

Aromatic conversion processes which are carried out over molecular sieve catalyst are well known in the chemical processing industry. Such aromatic conversion reactions include the alkylation of aromatic substrates such as benzene to produce alkyl aromatics such as ethylbenzene, ethyltoluene, cumene or higher aromatics and the transalkylation of polyalkyl benzenes to monoalkyl benzenes. Typically, an alkylation reactor which produces a mixture of mono- and poly-alkyl benzenes may be coupled through various separation stages to a downstream transalkylation reactor. Such alkylation and transalkylation conversion processes can be carried out in the liquid phase, in the vapor phase or under conditions in which both liquid and vapor phases are present.

Alkylation and transalkylation reactions may occur simultaneously within a single reactor. For example, where various series-connected catalyst beds are employed in an alkylation reactor as described below, it is a conventional practice to employ interstage injection of the aromatic substrate between the catalyst beds, which tends to enhance transalkylation reactions within the alkylation reactor. For example, in the ethylation of benzene with ethylene to produce ethylbenzene, the alkylation product within the reactor includes not only ethylbenzene but also polyethylbenzene, principally diethylbenzene with reduced amounts of triethylbenzene, as well as other alkylated aromatics such as cumene and butylbenzene. The interstage injection of the ethylene results not only further in alkylation reactions but also transalkylation reactions where, for example, benzene and diethylbenzene undergo transalkylation to produce ethylbenzene. Thus, even though a separate transalkylation reactor is connected downstream through a series of separation stages, it is the accepted practice to minimize polyalkylation within the alkylation reactor in order to facilitate the subsequent treatment and separation steps.

An example of vapor phase alkylation is found in U.S. Pat. No. 4,107,224 to Dwyer. Here, vapor phase ethylation of benzene over a zeolite catalyst is accomplished in a down flow reactor having four series connected catalyst beds. The output from the reactor is passed to a separation system in which ethylbenzene product is recovered, with the recycle of polyethylbenzenes to the alkylation reactor where they undergo transalkylation reactions with benzene. The Dwyer catalysts are characterized in terms of those having a constraint index within the approximate range of 1–12 and include, with the constraint index in parenthesis, ZSM-5 (8.3), ZSM-11(8.7), ZSM-12(2), ZSM-35(4.5), ZSM-38(2), and similar materials.

A silicalite is a well-known alkylation catalyst. For example, U.S. Pat. No. 4,520,220 to Watson et al discloses the use of silicalite catalysts having an average crystal size of less than 8 microns and a silica/alumina ratio of at least about 200 in the ethylation of an aromatic substrate such as benzene or toluene to produce ethylbenzene or ethyltoluene, respectively. As disclosed in Watson et al, the alkylation procedure can be carried out in a multi-bed alkylation reactor at temperatures ranging from about 350°–500° C. and, more desirably, about 400°–475° C., with or without a steam co-feed. The reactor conditions in Watson et al are such as provide generally for vapor phase alkylation conditions.

Another procedure employing silicalite and involving the ethylation of benzene under vapor phase reaction conditions coupled with the recycle of polyethylbenzene containing products back to the alkylation reactor is disclosed in U.S. Pat. No. 4,922,053 to Wagnespack. Here, alkylation is carried out at temperatures generally in the range of 370° C. to about 470° C. and pressures ranging from atmospheric up to about 25 atmospheres over a catalyst such as silicalite or ZSM-5. The catalysts are described as being moisture sensitive and care is taken to prevent the presence of moisture in the reaction zone. The alkylation/transalkylation reactor comprises four series connected catalyst beds. Benzene and ethylene are introduced into the top of the reactor to the first catalyst bed coupled by recycle of a polyethylbenzene fraction to the top of the first catalyst bed as well as the interstage injection of polyethylbenzene and benzene at different points in the reactor.

Another process involving the use of a silicalite as an alkylation catalyst involves the alkylation of an alkylbenzene substrate in order to produce dialkylbenzene of a suppressed ortho isomer content. Thus, as disclosed in U.S. Pat. No. 4,489,214 to Butler et al, silicalite is employed as a catalyst in the alkylation of a monoalkylated substrate, toluene or ethylbenzene, in order to produce the corresponding dialkylbenzene, such as toluene or diethylbenzene. Specifically disclosed in Butler et al is the ethylation of toluene to produce ethyltoluene under vapor phase conditions at temperatures ranging from 350°–500° C. As disclosed in Butler, the presence of ortho ethyltoluene in the reaction product is substantially less than the thermodynamic equilibrium amount at the vapor phase reaction conditions employed.

U.S. Pat. No. 4,185,040 to Ward et al discloses an alkylation process employing a molecular sieve catalyst of low sodium content which is said to be especially useful in the production of ethylbenzene from benzene and ethylene and cumene from benzene and propylene. The $Na_2O$ content of the zeolite should be less than 0.5 wt. %. Examples of suitable zeolites include molecular sieves of the X, Y, L, B, ZSM-5, and omega crystal types, with steam stabilized hydrogen Y zeolite being preferred. Specifically disclosed is a steam stabilized ammonium Y zeolite containing about 0.2% $Na_2O$. Various catalyst shapes are disclosed in the Ward et al patent. While cylindrical extrudates may be employed, a particularly preferred catalyst shape is a so-called "trilobal" shape which is configured as something in the nature of a three leaf clover. The surface area/volume ratio of the extrudate should be within the range of 85–160 in.$^{-1}$. The alkylation process may be carried out with either upward or downward flow, the latter being preferred, and preferably under temperature and pressure conditions so that at least some liquid phase is present, at least until substantially all of the olefin alkylating agent is consumed. Ward et al states that rapid catalyst deactivation occurs under most alkylating conditions when no liquid phase is present.

U.S. Pat. No. 4,169,111 to Wight discloses an alkylation/transalkylation process for the manufacture of ethylbenzene employing crystalline aluminosilicates in the alkylation and transalkylation reactors. The catalysts in the alkylation and transalkylation reactors may be the same or different and include low sodium zeolites having silica/alumina mole ratios between 2 and 80, preferably between 4–12. Exemplary zeolites include molecular sieves of the X, Y, L, B, ZSM-5 and omega crystal types with steam stabilized Y zeolite containing about 0.2% $Na_2O$ being preferred. The alkylation reactor is operated in a downflow mode and under temperature and pressure conditions in which some liquid phase is present. The output from the alkylating reactor is cooled in a heat exchanger and supplied to a benzene separation column from which benzene is recovered overhead and recycled to the alkylation reactor. The initial higher boiling bottoms fraction from the benzene column comprising ethylbenzene and polyethylbenzene is supplied to an initial ethylbenzene column from which the ethylbenzene is recovered as the process product. The bottoms product from the ethylbenzene column is supplied to a third column which is operated to provide a substantially pure diethylbenzene overheads fraction which contains from 10 to 90%, preferably 20 to 60% of diethylbenzene. The diethylbenzene overheads fraction is recycled to the alkylation reactor while a side cut containing the remaining diethylbenzene and triethylbenzene and higher molecular weight compounds is supplied to the reactor along with benzene. The effluent from the reactor is recycled through the heat exchanger to the benzene column.

U.S. Pat. No. 4,774,377 to Barger et al discloses an alkylation/transalkylation process which, involves the use of separate alkylation and transalkylation reaction zones, with recycle of the transalkylated product to an intermediate separation zone. In the Barger process, the temperature and pressure conditions are adjusted so that the alkylation and transalkylation reactions take place in essentially the liquid phase. The transalkylation catalyst is an aluminosilicate molecular sieve including X-type, Y-type, ultrastable-Y, L-type, omega type and mordenite type zeolites with the latter being preferred. The catalyst employed in the alkylation reaction zone is a solid phosphoric acid containing material. Aluminosilicate alkylation catalysts may also be employed and water varying from 0.01 to 6 volume percent is supplied to the alkylation reaction zone. The output from the alkylation reaction zone is supplied to first and second separation zones. Water is recovered in the first separation zone. In the second separation zone, intermediate aromatic products and trialkylaromatic and heavier products are separated to provide an input to the transalkylation reaction zone having only dialkyl aromatic components, or diethylbenzene in the case of an ethylbenzene manufacturing procedure or diisopropylbenzene in the case of cumene production. A benzene substrate is also supplied to the transalkylation zone for the transalkylation reaction and the output from the transalkylation zone is recycled to the first separation zone. The alkylation and transalkylation zones may be operated in downflow, upflow, or horizontal flow configurations.

EPA publication 467,007 to Butler discloses other processes having separate alkylation and transalkylation zones employing various molecular sieve catalysts and with the output from the transalkylation reactor being recycled to an intermediate separation zone. Here, a benzene separation zone, from which an ethylbenzene/polyethylbenzene fraction is recovered from the bottom with recycling of the overhead benzene fraction to the alkylation reactor is preceded by a prefractionation zone. The prefractionation zone produces an overhead benzene fraction which is recycled along with the overheads from the benzene column and a bottom fraction which comprises benzene, ethylbenzene and polyethylbenzene. Two subsequent separation zones are interposed between the benzene separation zone and the transalkylation reactor to provide for recovery of ethylbenzene as the process product and a heavier residue fraction. The polyethylbenzene fraction from the last separation zone is applied to the transalkylation reactor and the output there is applied directly to the second benzene separation column or indirectly through a separator and then to the second benzene separation column. Butler discloses that the alkylation reactor may be operated in the liquid phase with a catalyst such as zeolite-$\beta$, zeolite-Y or zeolite-$\Omega$ or in the vapor phase employing a catalyst such as silicalite or ZSM-5. In the Butler process, where vapor phase alkylation is followed by liquid phase transalkylation, substantial quantities of water may be included in the feedstream to the alkylation reactor. In this case, the feed to the transalkylation reactor may be dehydrated to lower the water content. The transalkylation catalyst may take the form of a zeolite-Y or zeolite-$\Omega$.

SUMMARY OF THE INVENTION

In accordance with the present invention there is provided a process for the production of ethylbenzene by alkylation over a silicalite alkylation catalyst with the subsequent transalkylation of diethylbenzene produced during the alkylation step. The silicalite alkylation catalyst and the alkylation conditions are selected in order to retard xylene production even at the expense of possibly enhanced diethylbenzene production. Moreover, the production of high molecular weight alkylaryl compounds, referred to sometimes simply as "heavies," can likewise be retarded in accordance with the present invention. The term, "heavies," as used herein, denotes the post-butylbenzene fraction of the reactor effluent, that is, the fraction boiling above about 185° C. The heavies content can be maintained at a value of no more than 0.25 wt. % based upon ethylbenzene in the product. In carrying out the invention a feedstock containing benzene and ethylene is applied to a multi-stage alkylation reaction zone having a plurality of series-connected catalyst beds containing a pentasil molecular sieve alkylation catalyst. The alkylation catalyst is silicalite of a predominantly monoclinic symmetry having a silica/alumina ratio of at least 275. The alkylation reaction zone is operated under pressure conditions to cause gas-phase ethylation of the benzene in the presence of the silicalite catalyst to produce a mixture of ethylbenzene and polyalkylated aromatics including triethylbenzene and diethylbenzene. The feedstock is supplied to the alkyllation reaction zone at a flow rate to provide a space velocity of benzene over the catalyst to produce a xylene concentration in the product of about 600 ppm or less based upon the ethylbenzene content. Periodically the space velocity may be increased to a value which is greater than the space velocity associated with a minimum concentration of diethylbenzene in the alkylation product. Thus, the space velocity is sufficiently high to deliberately enhance diethylbenzene production while minimizing any attendant transalkylation reactions within the alkylation reaction zone. This is accompanied by a relatively low xylene content in the product. More specifically, the average xylene concentration of the product in the course of the operation of the alkylation reactor is no more than 600 ppm based upon the ethylbenzene in the product. The output from the alkylation reactor is applied to an intermediate recovery zone for the separation and recovery of ethylbenzene. A polyalkylated aromatic component including diethylbenzene is recovered from the intermediate zone and supplied along with benzene to a transalkylation reaction zone where the polyalkylated aromatic fraction is subject to disproportionation to provide a reduced diethylbenzene content and an enhanced ethylbenzene content. Preferably, the monoclinic silicalite alkylation catalyst has a silica/alumina ratio of at least 300 and has a crystal size of less than one micron. The preferred catalyst has a crystal size of about 0.5 micron or less and is formulated with an alumina binder to provide catalyst particles having a surface/volume ratio of at least $60^{-1}$ inch.

DETAILED DESCRIPTION OF THE INVENTION

Figure 1:
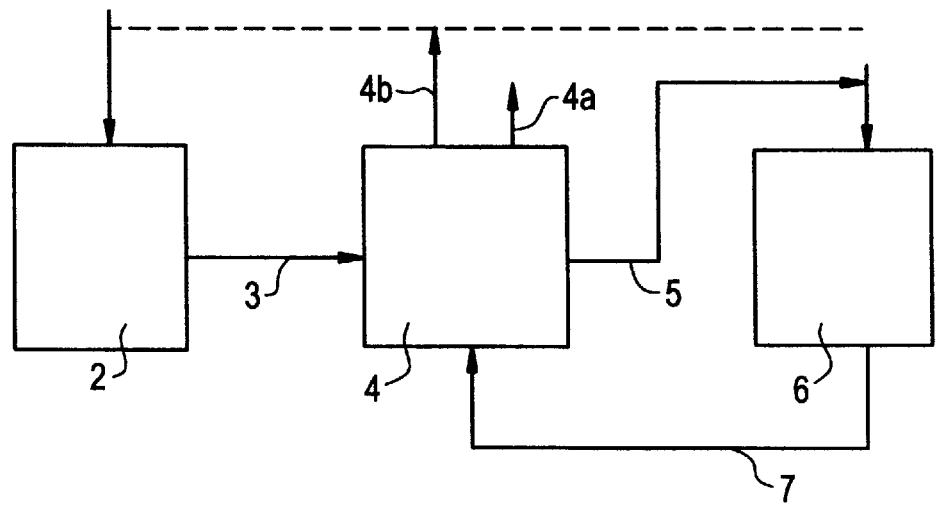
FIG. 1 is an idealized schematic block diagram of an alkylation/transalkylation process embodying the present invention.

The present invention follows the accepted practice of vapor-phase alkylation of an aromatic substrate in a multi-stage alkylation reaction zone followed by a separate transalkylation reaction. However, rather than operating the alkylation reactor in a mode to achieve both alkylation and transalkylation, thus minimizing the load ultimately placed on the transalkylation reactor, the present invention proceeds in a manner contrary to the normal prior art practice by employing a high silica/alumina ratio silicalite alkylation catalyst in a mode that actually increases the diethylbenzene output from the alkylation reaction during a portion of a cycle of operation in which one of a plurality of parallel reactors is placed in a regeneration mode. Here, the alkylation reactor is operated under a relatively high space velocity such that the alkylation over the silicalite catalyst is carried out to provide a diethylbenzene content substantially above what is achieved under normal operating conditions. Specifically, the diethylbenzene content is increased by incremental value of about 0.2 or more of the diethylbenzene content produced at a space velocity of one-half of the enhanced space velocity. This enhanced space velocity occurs during a relatively short period of time after which a reduced space velocity is encountered in which the diethylbenzene content is reduced during normal operating conditions to a value near the thermodynamic equilibrium value. The enhanced diethylbenzene production is offset by an accompanying selectivity toward the production of ethylbenzene relative to the production of xylenes as a by-product. Stated otherwise, the xylene content in the product is diminished preferably to a value of less than 600 ppm based upon the ethylbenzene in the product. Further, the ortho xylene content is contained at a relatively low level, less than the thermodynamic equilibrium level of ortho xylene at temperature and pressure conditions of the alkylation reactor zone. Specifically, the ortho xylene content can be diminished to a value of about one-half or less than the equilibrium value. In this respect the equilibrium ratio of the three isomers of xylene at a desired alkylation temperature of about 400° C. is 24.3% ortho xylene, 52.3% meta xylene, and 23.4% para xylene. The practice of the present invention can result in a ortho xylene content in the reaction product of no more than about 10 wt. % of the total xylene content of the reaction product.

The silicalite employed in the present invention, in addition to having a relative high silica aluminum ratio, has a somewhat smaller crystal size than the silicalite traditionally employed in aromatic alkylation procedures. Silicalite, as is well known in the art, is a molecular sieve catalyst which is similar to the ZSM-5 zeolites but is typically characterized by a higher silica/alumina ratio providing an aluminum unit cell ratio of less than 1, and, in addition, is normally characterized as having a somewhat larger than average crystal size than is commonly associated with the ZSM zeolites. As is well known in the art, silicalite, which in the as synthesized form is characterized by orthorhombic symmetry, can be converted to monoclinic symmetry by a calcination procedure as disclosed, for example, in U.S. Pat. No. 4,599,473 to DeBras et al. As described in detail in DeBras et al, "Physico-chemical characterization of pentasil type materials, I. Precursors and calcined zeolites, and II. Thermal analysis of the precursors," ZEOLITES, 1985, Vol. 5, pp. 369–383, the silicalite typically has a relatively large crystal size. Thus, at an average of less than one aluminum atom per unit cell (a silica/alumina ratio of about 200) silicalite typically has an average crystal size of perhaps 5–10 microns or more. The aforementioned U.S. Pat. No. 4,489,214 to Butler et al discloses experimental work involving the ethylation of toluene over silicalite or a crystal size greater than one micron, ranging from 1–2 microns up to 8 microns. The silicalite is further characterized in terms of a variable aluminum gradient such that the aluminum gradient is positive when going from the interior to the surface of the molecular sieve crystal. That is, the silicalite can be characterized by a core portion which is relatively aluminum deficient with an outer shell portion which is relatively aluminum rich. It is to be understood that the term "aluminum rich" is a relative term and that for silicalite even the outer shell portion of the crystallite has a low aluminum content.

The present invention involves vapor phase ethylation of benzene in a multistage reaction zone containing high silica/alumina ratio silicalite followed by liquid phase transalkylation in which the alkylation and transalkylation reactors are integrated with an intermediate recovery zone, preferably involving a plurality of separation zones operated in a manner to effectively provide feed streams to the reactors with recycle of the output from the transalkylation reactor to a benzene recovery zone downstream of the alkylation reactor. In this integrated mode of operation, the transalkylation product is applied to an initial stage of a benzene recovery zone. Subsequent separation steps are carried out in a manner to apply a split feed to the transalkylation reactor. The alkylation reactor is a multistage reaction zone containing at least three series connected catalyst beds which contain the silicalite alkylation catalyst, more preferably four or more beds are employed. As described in greater detail below, the silicalite alkylation catalyst preferably is silicalite characterized as having a high monoclinicity and a small sodium content. The preferred catalyst used in the transalkylation reactor is a molecular sieve having a pore size greater than the pore size of the silicalite catalyst. Preferably, the transalkylation catalyst is zeolite Y. As will be described in greater detail below, the alkylation reactor is preferably operated at substantially higher temperature conditions than the transalkylation reactor. In one embodiment of the invention, the recycled output from the transalkylation reactor is passed in a heat exchange relationship with the alkylation reactor product feed to the initial benzene separation zone.

A preferred application of the invention is in a system involving a multistage alkylation reactor with the output coupled to a four-stage separation system which in turn supplies a polyethylbenzene feed to a transalkylation reactor. In the embodiment of the invention described herein, parallel alkylation and transalkylation reactors are employed. This results in a preferred mode of operation in which the parallel alkylation reactors are simultaneously operated in an alkylation mode while periodically one reactor can be taken off-stream with the feedstream completely supplied to the on-stream reactor. In the embodiment illustrated and described below, two parallel reactors are employed although it is to be recognized that three or more reactors can likewise be employed in parallel. A similar configuration is employed for the transalkylation reactors. The result is that simultaneous catalyst regeneration can occur in one reactor during operation of the remaining alkylation and/or transalkylation reactors. Assuming that two parallel reactors are employed, it can be seen that this mode of operation will, for the same flow rate of feedstream, result in the operation of the reactors at two different space velocities, with the space velocity during regeneration of a reactor being about twice that with both parallel reactors in operation.

Preferably the alkylation reactor comprises at least four catalyst beds as described above. More beds can be provided, and it will sometimes be advantageous to provide at least five catalyst beds in the alkylation reactor. The reactor is operated so as to provide vapor phase alkylation (both the aromatic substrate and the alkylating agent are in the vapor phase) at temperatures ranging from about 630° F.–800° F. at the inlet to about 700° F.–850° F. at the outlet. The pressure may be within the range of about 250 to 450 psia with the pressure decreasing from one bed to the next as the temperature increases. By way of example, the benzene and ethylene supplied to the top of the reactor may enter the reactor at a temperature of about 740° F. and a pressure of about 430 psia. The alkylation reaction is exothermic so that the temperature progressively increases from the first to the last catalyst bed by a way of example. The interstage temperatures may increase from 750° F. for the first catalyst bed to 765° F. after the second catalyst bed to 820° F. after the third catalyst bed to a temperature of about 840° F. after the last catalyst bed.

Normally in the operation of multi-stage reaction zone of the type involved in the present invention, a benzene-ethylene mixture is introduced to the first catalyst bed at the top of the reaction zone and also in between the several successive stages of catalyst beds. In the present invention, ethylene is supplied along with benzene to the top of the first catalyst bed top at the upper end of the reactor. In addition, interstage injection of ethylene and benzene is provided for between the subsequent catalyst beds. The benzene to ethylene mole ratio is about 18 as injected into the top of the alkylation reactor and progressively decreases because of the interstage injection of ethylene and coupled with the alkylation of the benzene to ethylbenzene and polyethylbenzenes.

The silicalite alkylation catalyst employed in the present invention does not require the presence of water to stabilize the catalyst, so a water or steam co-feed, as is sometimes used in connection with silicalite, is not called for in this invention. As noted above, interstage injection of ethylene is normally employed, and the interstage injection of benzene can also be provided for. The mole ratio of the benzene to the ethylene at the interstage injection points can vary from zero (no benzene injection) up to about five. The benzene in many cases will be employed in an amount less than the amount of ethylene on a mole basis. Stated otherwise, benzene can either not be injected between the catalyst beds or, if injected, can be employed in a relatively minor amount, i.e., a mole ratio of benzene to ethylene of less than one. On the other hand, the benzene/ethylene mole ratio can be as high as five. This is coupled with a somewhat lower operating temperature than would normally be the case for vapor phase alkylation. In the preferred embodiment of the invention, the temperature of the benzene stream into the top of the alkylation reactor will be in the order of 720° F. or lower. The alkylation reaction is, of course, an exothermic reaction so that the temperature will be increased progressively throughout the alkylation column as noted previously.

The silicalite alkylation catalyst employed in the present invention is a molecular sieve from the pentasil family of high silica molecular sieves. Such pentasil molecular sieves are described, for example, in Kokotailo et al, "Pentasil Family of High Silica Crystalline Materials," Chem. Soc. Special Publ. 33, 133–139 (1980).

The silicalite molecular sieve alkylation catalyst has a somewhat smaller pore size than the preferred zeolite-Y employed in the transalkylation reactor. The silicalite catalyst has an effective pore size or window within the range of 5–6 angstroms. Zeolite Y has a pore size of about 7 angstroms. The preferred silicalite catalyst has a somewhat smaller crystal size, less than one micron, than is usually the case. Preferably, the crystal size is even somewhat smaller, about $0.5\mu$, as contrasted with a crystal sizes of perhaps $1-2\mu$ up to about 8 microns for similar catalysts such as disclosed in the aforementioned U.S. Pat. No. 4,489,214 to Butler et al.

A preferred silicalite for use in the present invention is extruded with an alumina binder in a "trilobe" shape having a nominal diameter of about 1/16" and a length of the extrudate of about 1/8–1/4". The "trilobe" cross sectional shape is something on the order of a three leaf clover. The purpose of this shape is to increase the surface area of the extruded catalyst beyond what one would expect with a normal cylindrical extrudate. The preferred silicalite catalyst is characterized as monoclinic silicalite. Monoclinic silicalite may be prepared as disclosed in U.S. Pat. Nos. 4,781,906 to Cahen et al and 4,772,456 to DeClippeleir et al. Preferably the catalysts will have near 100% monoclinicity) although silicalite catalysts that are 70–80% monoclinic and about 20–30% orthorhombic symmetry may be used in the preferred embodiment of the invention. The silicalite preferably is present in an amount of 75–80wt. % with the alumina binder being present in an amount of 20–25 wt. %. The silica/alumina ratio of the silicalite is at least 275 and preferably at least 300. An especially preferred silica/alumina ratio is 300–350, and silicalite within this range was used in experimental work respecting the invention as described hereafter. The silicalite may have an alpha value of about 20–30. The "alpha value" is characterized in terms of the activity of a catalyst for cracking hexane as disclosed in U.S. Pat. Nos. 4,284,529 to Shihabi and 4,559,314 to Shihabi. The catalyst typically contains small amounts of sodium and iron.

As noted previously, the silicalite alkylation catalyst has a crystal structure characterized by an aluminum rich outer shell and an aluminum deficient interior portion when compared with the outer shell. The silicalite catalyst is dry and has no appreciable or intended water content. The alumni binder is a high purity alumina such as "catapal alumina." The silicalite catalyst preferably contains only a small amount of sodium, about 70–200 ppm sodium oxide, and contains only a small amount of iron oxide, about 300–600 ppm. The catalyst need not contain any additional "promoter" metals incorporated during the synthesis of the catalyst.

Turning now to the drawings and referring first to FIG. 1, there is illustrated a schematic block diagram of an alkylation/transalkylation process carried out in accordance with the present invention. As shown in FIG. 1, a product stream comprising a mixture of ethylene and benzene in a mole ratio of benzene to ethylene about 10 to 20 supplied via line 1 to an alkylation zone 2. Alkylation zone 2 comprises one or more multi-stages reactor having a plurality of series-connected catalyst beds containing the preferred high silica/alumina ratio silicalite as described in greater detail below. The alkylation zone is operated at temperature and pressure conditions to maintain the alkylation reaction in the vapor phase, i.e. the aromatic substrate is in the vapor phase, and at a feed rate to provide a space velocity enhancing diethylbenzene production while retarding xylene production.

The output from the alkylation reactor is supplied via line 3 to an intermediate recovery zone 4 which provides for the separation and recovery of ethylbenzene as a product. Thus, ethylbenzene is withdrawn from zone 4 via line 4a and applied for any suitable purposes such as in the production of vinylbenzene. Recovery zone 4 normally will be characterized by a plurality of series-connected distillation columns as described below and will result in a heavy polyalkylated product stream which is supplied via line 5 to a transalkylation zone 6. Typically, benzene will also be recovered from the intermediate recovery zone via a line 4b. The benzene may be applied as indicated by the broken lines both for recycle back to the alkylation reactor and also to the transalkylation zone as may be appropriate. Within the transalkylation zone, the benzene and diethylbenzene undergo a disproportionation reaction resulting in a product of enhanced ethylbenzene content and diminished benzene and diethylbenzene content. Typically, the output from the transalkylation zone will be supplied via line 7 for recycle to the separation zone 4.

Figure 2A:
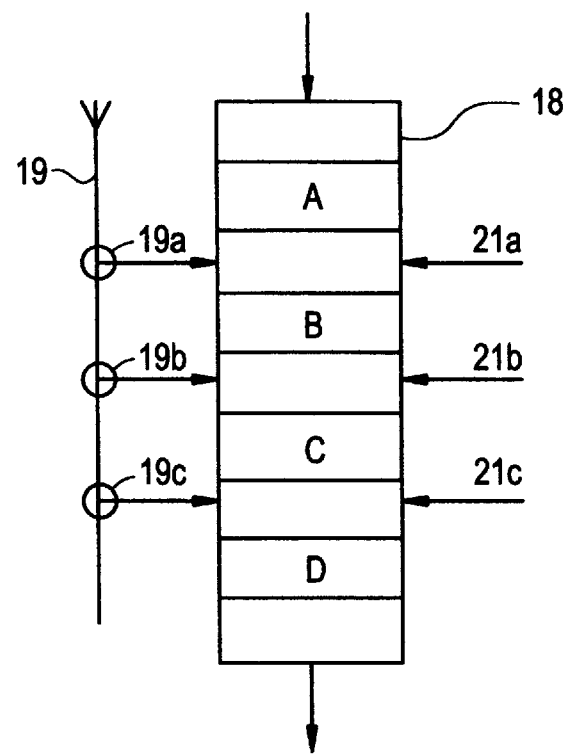
FIG. 2A is a schematic illustration of an alkylation zone comprising a plurality of series-connected catalyst beds with the interstage injection of feed components.
Figure 2:
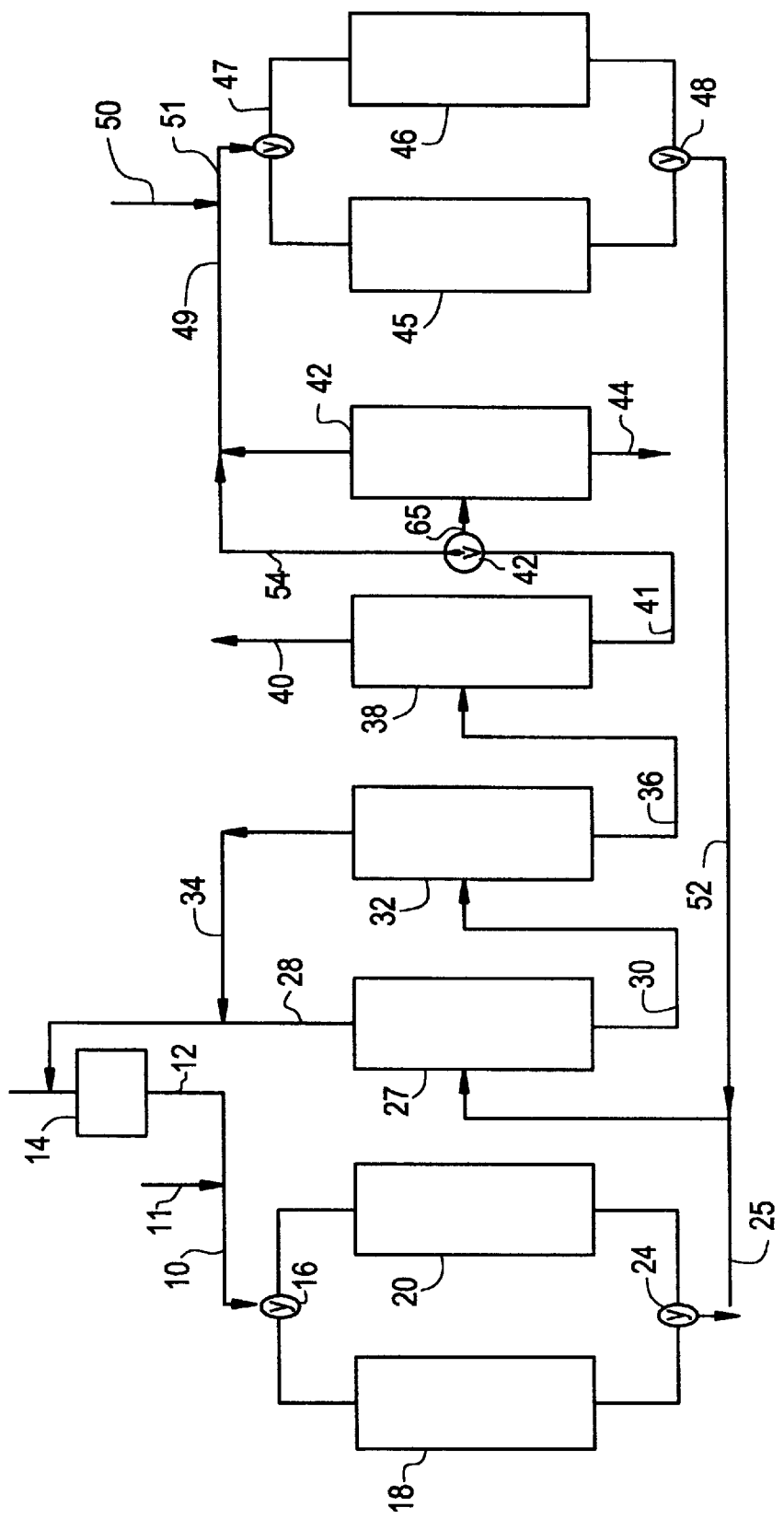
FIG. 2 is a schematic illustration of a preferred embodiment of the invention incorporating separate parallel-connected alkylation and transalkylation reactors with an intermediate multi-stage recovery zone for the separation and recycling of components.

Referring now to FIG. 2, there is illustrated in greater detail a suitable system incorporating a multi-stage intermediate recovery zone for the separation and recycling of components involved in the alkylation/transalkylation process. As shown in FIG. 2, an input feed stream is supplied by fresh ethylene through line 11 and fresh benzene through line 12. Line 12 is provided with a preheater 14 to heat the benzene stream to the desired temperature for the alkylation reaction. The feedstream is applied through a two-way, three-position valve 16 and inlet line 10 to the top of one or both parallel alkylation reaction zones 18 and 20 comprising a plurality of series connected catalyst beds each of which contains a silicalite alkylation catalyst. The reactors are operated at an average temperature, preferably within the range of 700° F.–800° F. and at pressure conditions of about 200 to 350 psia, to maintain the benzene in the gaseous phase.

In normal operation of the system depicted in FIG. 2, both reaction zones 18 and 20 will, during most of a cycle of operation, be operated in a parallel mode of operation in which they are both in service at the same time. In this case, valve 16 is configured so that the input stream in line 10 is roughly split to provide flow to both reactors in approximately equal amounts. Periodically, one reactor can be taken off-stream for regeneration of the catalyst. Valve 16 is configured so that all of the feedstream from line 10 can be supplied to reactor 18 while the catalyst beds in reactor 20 are regenerated and visa versa. The regeneration procedure will be described in detail below but normally will take place over a relatively short period of time relative to the operation of the reactor in parallel alkylation mode. When regeneration of the catalyst beds in reactor 20 is completed, this catalyst can then be returned on-stream, and at an appropriate point, the reactor 18 can be taken off-stream for regeneration. This mode of operation in operation of the individual catalyst beds at relatively lower space velocities for prolonged periods of time with periodic relatively short periods of operation at enhanced, relatively higher space velocities when one reactor is taken off-stream. By way of example, during normal operation of the system with both reactors 18 and 20 on-stream, the feedstream is supplied to each reactor to provide a space velocity of about 35 hr.$^{-1}$ LHSV. When reactor 20 is taken off-stream and the feed rate continues unabated, the space velocity for reactor 18 will approximately double to 70 hr.$^{-1}$ LHSV. When the regeneration of reactor 20 is completed, it is placed back on-stream, and again the flow rate space velocity for each reactor will decrease to 35 hr.$^{-1}$ until such point as reactor 18 is taken off-stream, in which the case the flow rate to reactor 20 will, of course, increase, resulting again in a transient space velocity in reactor 20 of 70 hr.$_{-1}$ LHSV.

A preferred reactor configuration is shown in detail in FIG. 2A. As illustrated there, the reactor 18 comprises four series connected catalyst beds designated as beds A, B, C and D. An ethylene feed stream is supplied via line 19 and proportionating valves 19a, 19b and 19c to provide for the appropriate interstage injection of ethylene. Benzene can also be introduced between the catalyst stages by means of secondary benzene supply lines 21a, 21b and 22b, respectively. As will be recognized, the parallel reactor 20 will be configured with similar manifolding as shown in FIG. 2A with respect to reactor 18.

Returning to FIG. 2, the effluent stream from one or both of the alklation reactors 18 and 20 is supplied through a two-way, three-position outlet valve 24 and outlet line 25 to a two-stage benzene recovery zone which comprises as the first stage a prefractionation column 27. Column 27 is operated to provide a light overhead fraction including benzene which is supplied via line 28 to the input side of heater 14 where it is mixed with benzene in line 12 and then to the alkylation reactor input line 10. A heavier liquid fraction containing benzene, ethylbenzene and polyethylbenzene is supplied via line 30 to the second stage 32 of the benzene separation zone. Stages 27 and 32 may take the form of distillation columns of any suitable type, typically, columns having from about 20–60 trays. The overheads fraction from column 32 contains the remaining benzene which is recycled via line 34 to the alkylation reactor input. Thus, line 34 corresponds to the output line 4b of FIG. 1. The heavier bottoms fraction from column 32 is supplied via line 36 to a secondary separation zone 38 for the recovery of ethylbenzene. The overheads fraction from column 38 comprises relatively pure ethylbenzene which is supplied to storage or to any suitable product destination by way of line 40, corresponding generally to output line 4a of FIG. 1. By way of example, the ethylbenzene may be used as a feedstream to a styrene plant in which styrene is produced by the dehydrogenation of ethylbenzene. The bottoms fraction containing polyethylbenzenes, heavier aromatics such as cumene and butylbenzene, and normally only a small amount of ethylbenzene is supplied through line 41 to a tertiary polyethylbenzene separation zone 42. As described below, line 41 is provided with a proportioning valve 43 which can be used to divert a portion of the bottoms fraction directly to the transalkylation reactor. The bottoms fraction of column 42 comprises a residue which can be withdrawn from the process via line 44 for further use in any suitable manner. The overhead fraction from column 42 comprises a polyalkylated aromatic component containing diethylbenzene and triethylbenzene (usually in relatively small quantities) and a minor amount of ethylbenzene is supplied to an on stream transalkylation reaction zone. Similarly as described above with respect to the alkylation reactors, parallel transalkylation reactors 45 and 46 are provided through inlet and outlet connections involving valves 47 and 48. Both of reactors 45 and 46 can be placed on stream at the same time so that both are in service in a parallel mode of operation. Alternatively, only one transalkylation reactor can be on-stream with the other undergoing regeneration operation in order to burn coke off the catalyst beds by minimizing the amount of ethylbenzene recovered from the bottom of column 38, the ethylbenzene content of the transalkylation feedstream can be kept small in order to drive the transalkylation reaction in the direction of ethylbenzene production. The polyethylbenzene fraction withdrawn overhead from column 42 is supplied through line 49 and mixed with benzene supplied via line 50. This mixture is then supplied to the on-line transalkylation reactor 45 via line 51. Preferably, the benzene feed supplied via line 50 is of relatively low water content, about 0.05 wt. % or less. Preferably, the water content is reduced to a level of about 0.02 wt. % or less and more preferably to no more than 0.01 wt. %. The transalkylation reactor is operated as described before is order to maintain the benzene and alkylated benzenes within the transalkylation reactor in the liquid phase. Typically, the alkylation reactor and the transalkylation reactor may be operated to provide an average temperature within the transalkylation reactor of about 150° F.–550° F. and an average pressure of about 600 psi. The preferred catalyst employed in the transalkylation reactor is zeolite Y having the characteristics described previously. The weight ratio of benzene to polyethylbenzene should be at least 1:1 and preferably is within the range of 1:1 to 4:1.

The output from the transalkylation reactor containing benzene, ethylbenzene and diminished amounts of polyethylbenzene is supplied via line 52 to the initial stage of the benzene recovery zone. This mode of operation is contrary to the normal mode of operation as disclosed in the aforementioned EPA 467,007 to Butler. As disclosed there, the output from the transalkylation reactor is supplied to the second stage of the benzene recovery zone, corresponding to column 32 in FIG. 2. While this mode of operation can be followed in carrying out the present invention, it is preferred to operate, as shown in FIG. 2, in which the transalkylation reactor output is supplied to the initial stage 27 of the benzene recovery zone. This offers the advantage of having a stream with approximately the same benzene and ethylbenzene composition as the stream from the alkylation reaction.

In the mode of operation described thus far, the entire bottoms fraction from the ethylbenzene separation column 38 is applied to the tertiary separation column 42 with overhead fractions from this zone then applied to the transalkylation reactor. This mode of operation offers the advantage of relatively long cycle lengths of the catalyst in the transalkylation reactor between regeneration of the catalyst to increase the catalyst activity. Another embodiment of the invention achieves this advantage by supplying a portion of the output from the ethylbenzene separation column through valve 43 directly to the transalkylation reactor. Surprisingly, by employing vapor phase alkylation coupled with liquid phase transalkylation in accordance with the present invention, a significant quantity of the bottoms fraction from the ethylbenzene column can be sent directly to the transalkylation reactor, thus decreasing the amount of residue which is lost from the process. This mode of operation is consistent with and particularly advantageous in combination with the operation of the alkylation reactor to retard transalkylation and enhance ethylbenzene production. While applicants' invention is not to be limited by theory, it is believed that direct application of a substantial portion of the output from the ethylbenzene separation zone to the transalkylation reactor is made possible, at least in part, by the low water content in the process stream resulting from low water content introduced initially into the transalkylation reactor.

As shown in FIG. 2, a portion of the bottoms fraction from the secondary separation zone 38 bypasses column 42 and is supplied directly to the transalkylation reactor 45 via valve 43 and line 54. A second portion of the bottoms fraction from the ethylbenzene column is applied to the tertiary separation column 42 through valve 43 and line 55. The overhead fraction from column 42 is commingled with the bypass effluent in line 54 and the resulting mixture is fed to the transalylation reactor via line 47. By bypassing the column 42 with a substantial portion of the bottoms product from column 38, the residue which is lost from the system can be reduced. Preferably in this mode of operation a substantial amount of the bottoms product from column 38 is sent directly to the transalkylation reactor, bypassing the polyethylbenzene column 42. Normally, the weight ratio of the first portion supplied via line 54 directly to the transalkylation reactor to the second portion supplied initially via line 55 to the polyethylbenzene would be within the range of about 1:2 to about 2:1. However, the relative amounts may vary more widely to be within the range of a weight ratio of the first portion to the second portion in a ratio of about 1:3 to 3:1.

In experimental work respecting the invention, alkylation was carried out over a preferred form of silicalite catalyst at a first relatively low space velocity favoring transalkylation in the alkylation reactor and at a second relatively high space velocity exemplifying operation in accordance with the present invention to retarding transalkylation and enhancing diethylbenzene production. All of the experimental work was carried out in a single pass reactor operated at an inlet temperature of 400° C. (752° F.) and a pressure of 300 psig. In all of the experimental work, the benzene feed had a purity in excess of 99%, an ethylbenzene content varying from about 0.2–0.7%, a non-aromatic content of about 0.1% or less, or other aromatic, principally toluene and $C_3$–$C_4$ alkylbenzene of about 0.1 wt. % or less. The benzene feed was supplied to the reactor at two flow rates, one providing a liquid hourly space velocity (LHSV) of 70 hr.$^{-1}$ and the other at 35 LHSV hr.$^{-1}$.

The silicalite catalyst employed in this experimental work was a predominantly monoclinic silicalite having a silica/alumina ratio of about 320. This catalyst (designated herein as Catalyst B) was extruded with an alumina binder (about 20 wt. %) in a trilobe configuration as described above. A second silicalite catalyst (Catalyst A) used in the experimental work was very similar to Catalyst B except this silicalite had a silica/alumina ratio of about 225. Catalyst A was likewise used at LHSV of 35 and 70 hr.$^{-1}$. Both the high and low silica/alumina ratio silicalite catalyst employed in the experimental work were monoclinic silicalite extruded with an alumina binder in a trilobe shape as described previously.

The results of this experimental work are set forth in FIGS. 3–8, which illustrate the experimental results in terms of various effluent component characteristics plotted on the ordinate versus the time in days plotted on the abscissa. In each of FIGS. 3–7 the time of the run "D," and thus the age of the catalyst in days since the inception of the run, is plotted on the abscissa. In FIGS. 3–7, the results over the lower silica/alumina ratio catalyst, Catalyst A, are shown in broken lines. Runs carried out with the higher silica/alumina ratio catalyst of the type employed in the present invention are indicated by solid lines with space velocities of 35 hr.$^{-1}$ and 70 hr.$^{-1}$.

In FIGS. 3–7, data points associated with the experimental work carried out over the lower silica/alumina ratio Catalyst A at 35 hr.$^{-1}$ LHSV are indicated by the symbol ■. Data points for this same catalyst at 70 hr.$_{-1}$ LHSV are indicated by the symbol □. The experimental work carried out over the high silica/alumina Catalyst B at 35 hr.$^{-1}$ LHSV is indicated by the symbol Δ. In FIGS. 3–7 curves illustrative of data for Catalyst A incorporate "A," e.g. curve A1 as in FIG. 3 and curve 4A1 as in FIG. 4, and for Catalyst B the legene "B," e.g. curve 4B1 in FIG. 4.

Two test runs were carried out over fresh catalysts having the high silica/alumina ratio at 70 hr.$^{-1}$ LHSV and the data points for these runs are indicated by the symbols ▲ (Test 2) and ◊ (Test 3). The catalyst employed in Test 3 was regenerated by burning coke off of the catalyst particles and was used again at a space velocity of 70 hr.$^{-1}$ LHSV. The regeneration procedure involved the intial injection of an air/nitrogen mixture having a total oxygen content initially of about 4 vol. % at a temperature of about 380°–420° C. Regeneration lasted for about six hours during which time the amount of nitrogen in the air/nitrogen mixture was progressively decreased until pure air (about 20% oxygen) was injected during the latter stages of the regeneration run. The regeneration step was carried out at a pressure of 450°–500° C. The results of the work with this regenerated catalyst are indicated by the symbol ○.

Figure 3:
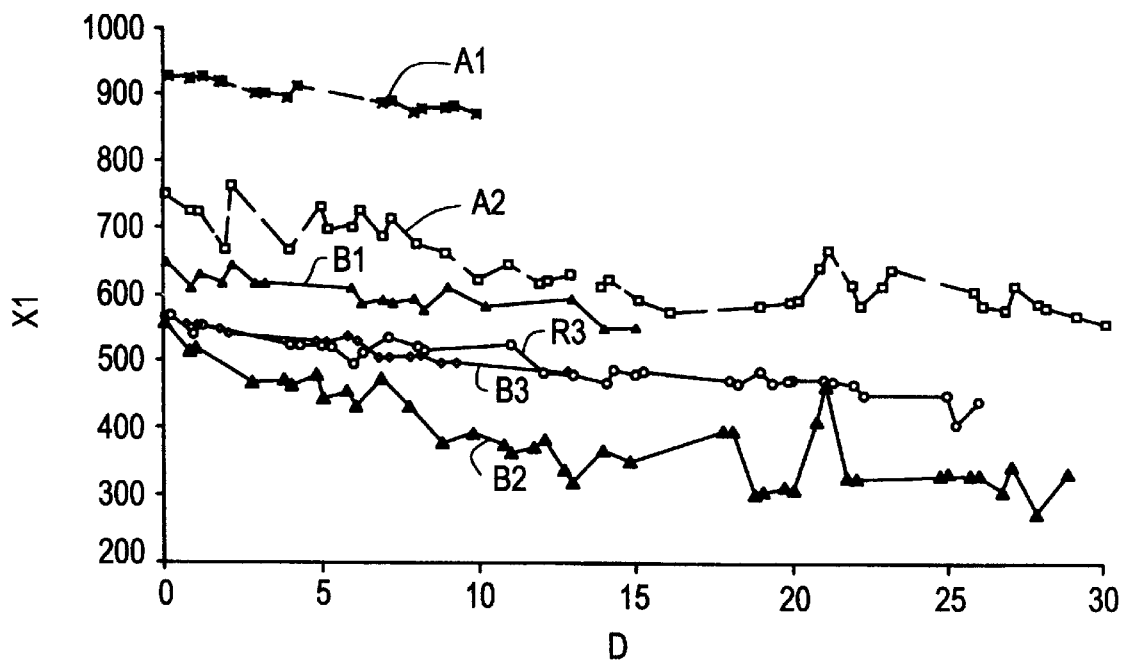
FIG. 3 is a graphical presentation showing the results of the experimental work and illustrating the xylene content relative to ethylbenzene for various silicalite catalysts at different space velocities as a function of time.

Referring first to FIG. 3, the xylene content (Xl) of the effluent relative to the ethylbenzene content measured in parts per million of xylene is plotted on the ordinate. In FIG. 3, the test run carried out with the lower silica/alumina ratio Catalyst A at the lower space velocity of 35 hr.$_{-1}$ LHSV is designated by the broken line curve A1. The corresponding test on the higher silica/alumina ratio Catalyst B at 35 hr.$_{-1}$ LHSV is indicated by the corresponding solid line curve B1. By increasing the space velocity over Catalyst A to 70 hr.$_{-1}$ indicated by Curve A-2, the xylene content was decreased substantially but still remained above the xylene content achieved with Catalyst B at the lower space velocity. The date given for xylene content in the product, as well as for the various other by-products, are presented in terms of the amount of ethylbenzene in the product. The ethylbenzene content in the reactor effluent typically will be about 12 wt. %. Thus, data presented in terms of 600 ppm (or 0.06 wt. %) relative to ethylbenzene would be equivalent to about 70 ppm xylene in the total reactor effluent.

Thus, the high silica/alumina ratio Catalyst B consistently produced lower xylenes content in the effluent than Catalyst A. By increasing the space velocity for Catalyst B from 35 to 70 hr.$^{-1}$ LHSV (Curves B2 and B3), even lower xylenes contents were achieved. When the catalyst used in Run 3 was regenerated and again used at an LHSV of 70 hr.$^{-1}$, (Curve R3), the xylene content was substantially the same as that achieved with the fresh catalyst.

Figure 4:
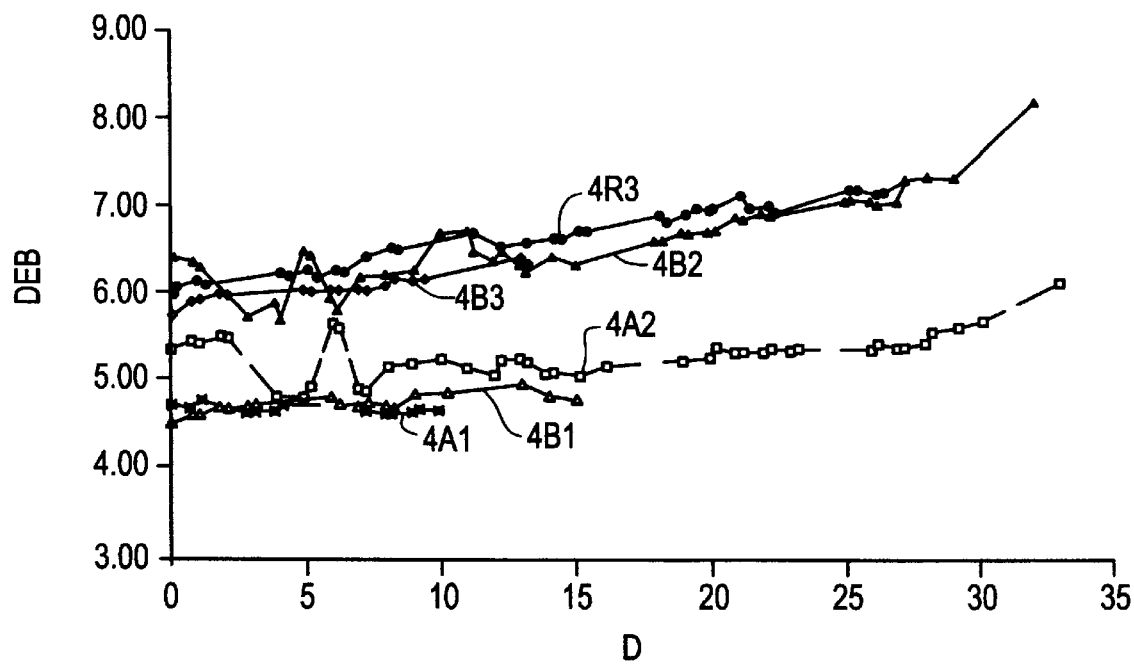
FIG. 4 is a graphical presentation to indicate the amount of diethylbenzene relative to ethylbenzene for various catalysts and space velocities as a function of time.

FIG. 4 illustrates the diethylbenzene content (DEB) in weight percent relative to the ethylbenzene content plotted on the ordinate versus the time in days (D) plotted on the abscissa. As shown in FIG. 4, by curves 4A1 and 4B1 for Catalysts A and B respectively at 35 hr.$_{-1}$ LHSV, both catalysts produced substantially the same diethylbenzene content, indicating that transalkylation occurred during the test runs at the lower space velocity. When the space velocity was increased for Catalyst B to 70 hr.$^{-1}$, substantially higher diethylbenzene contents were observed. This was observed in both test runs of the fresh Catalyst B and also in the Catalyst B used in the second test run in which Catalyst B was regenerated, as indicated by curves 4B2, 4B3, and 4R3. The incremental increase in diethylbenzene content when going from a space velocity of 35 to 70 hr.$^{-1}$ is, as shown in FIG. 4, about 0.2 of the space velocity at 35 hr.$^{-1}$. Stated otherwise, the ratio of the diethylbenzene content produced at a space velocity of 70 hr.$^{-1}$ to the diethylbenzene content produced at one-half of this space velocity level (35 hr.$^{-1}$) is shown initially to be about 1.2. With time and aging during the use of the high silica/alumina ratio catalyst, this ratio appears to increase somewhat, for example, to a value of about 1.3 at a catalyst age of 10 days. On the other hand, when the space velocity for the lower silica/alumina ratio Catalyst A was doubled from 35 to 70 hr.$^{-1}$ LHSV, as indicated by curve 4A2, only a modest increase in diethylbenzene content was observed. This indicated significant transalkylation activity over the lower silica/alumina ratio catalyst even at the higher space velocity. For the higher silica/alumina ratio Catalyst B, on the other hand, the transalkylation activity diminished substantially resulting in a substantially higher diethylbenzene content.

Figure 5:
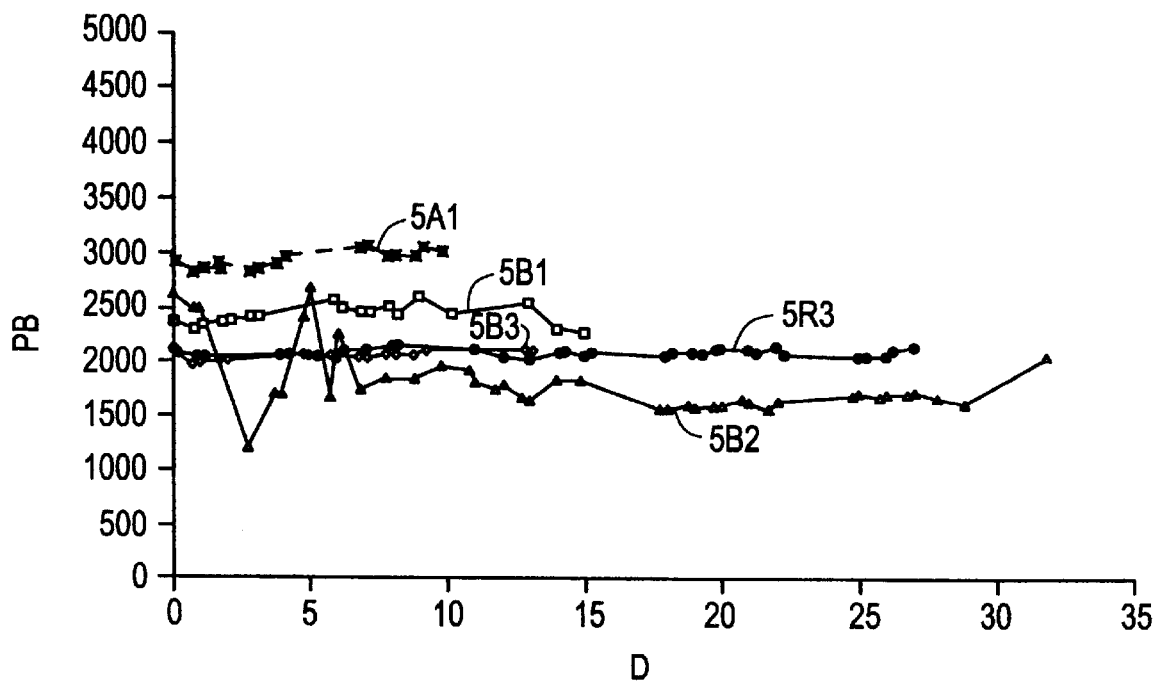
FIG. 5 is a graphical presentation showing the relative amount of propylbenzene relative to ethylbenzene as a function of time for the various catalysts and space velocities.
Figure 6:
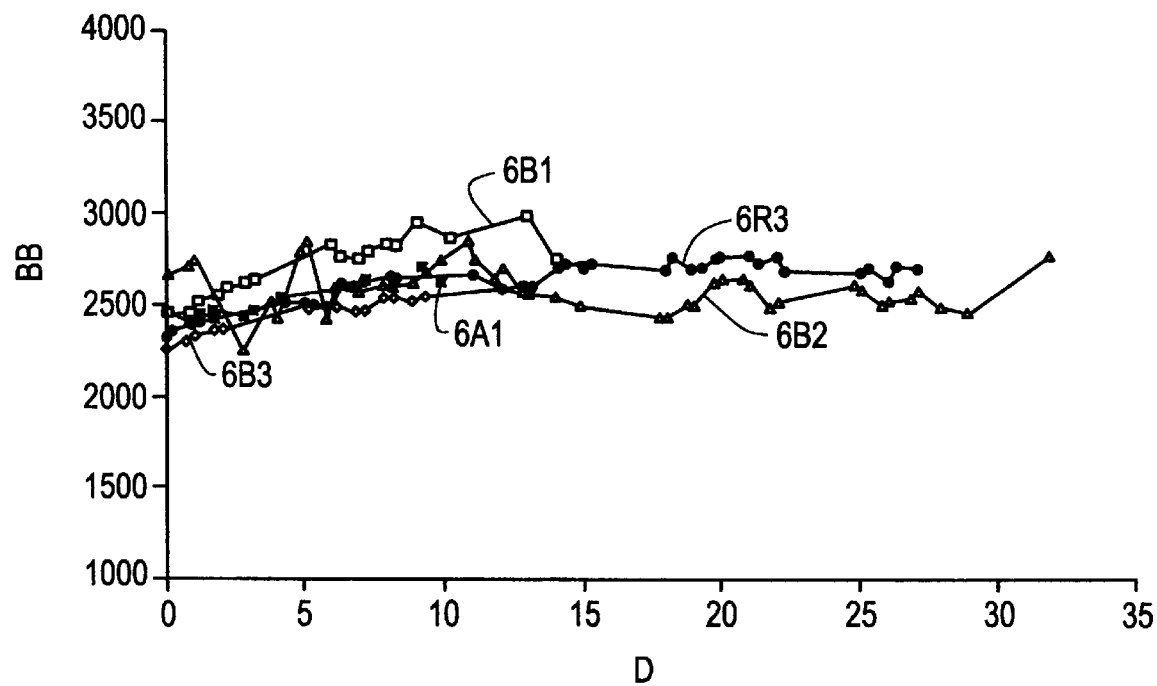
FIG. 6 is a graphical presentation showing the relative amount of butylbenzene relative to ethylbenzene for the different catalysts and space velocities as a function of time.

FIG. 5 illustrates the results of the experimental work in terms of propylbenzene content (PB) in parts per million relative to ethylbenzene versus the catalyst age in days (D). Corresponding values of the butylbenzene content (BB) relative to ethylbenzene are shown in weight parts per million on the ordinate of FIG. 6. As indicated by FIG. 5, Catalyst B (curve 5B1) showed somewhat lower propylbenzene content in the effluent than Catalyst A (curve 5A1) at the lower space velocity of 35 hr.$^{-1}$ LHSV. At the higher space velocity of 70 hr.$^{-1}$, Catalyst B in both tests showed generally somewhat lower propylbenzene content than at the higher space velocities, as indicated by curves 5B2 and 5B3. This was true for the regenerated catalyst (curve RB3) at the higher space velocity. Referring to FIG. 6, at space velocity of 35 hr.$_{-1}$ the higher silica/alumina ratio Catalyst B (curve 6B1) showed slightly higher butylbenzene content than was observed for Catalyst A (curve 6A1). Space velocity appeared to show very little effect on the butylbenzene made for the Catalyst B.

Figure 7:
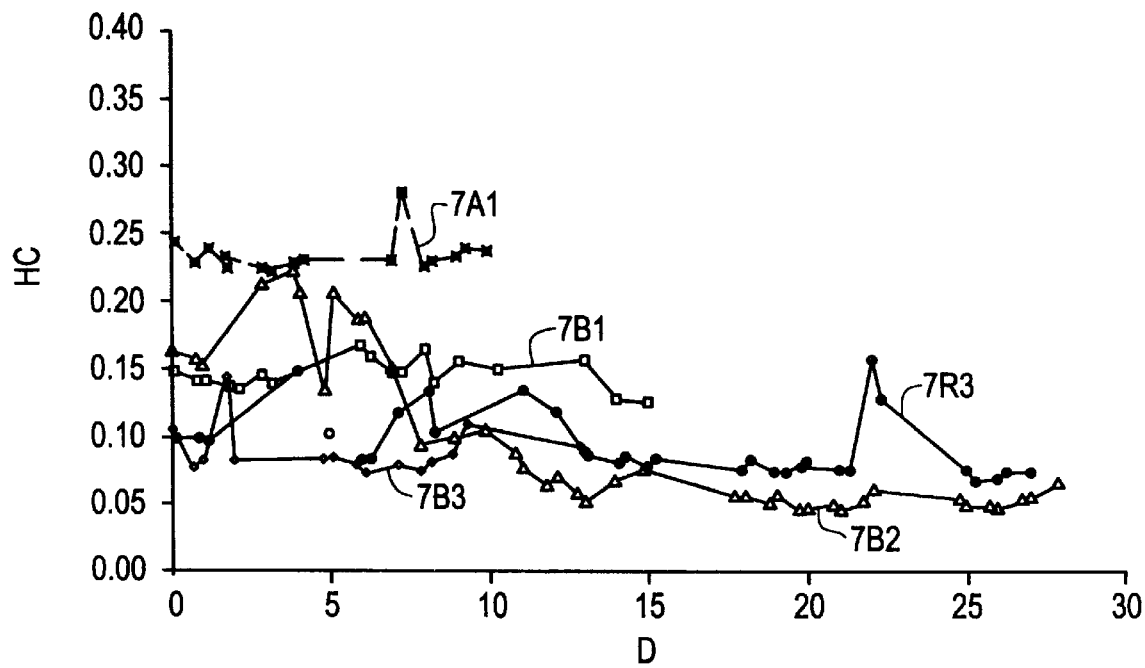
FIG. 7 is a graphical presentation of the amount of heavies content relative to ethylbenzene as a function of time for the various catalysts and space velocities.

In FIG. 7 the heavies content (HC) in weight percent relative to ethylbenzene is charted on the ordinate versus the catalyst age (D) in days on the abscissa. As shown in FIG. 7, the higher silica/alumina ratio Catalyst B (curve 7B1) showed substantially lower heavies content relative to ethylbenzene at an LHSV of 35 hr.$^{-1}$ than for Catalyst A (curve 7A1). The heavies content was generally further reduced by operating with Catalyst B at the higher space velocity. The heavies content was generally considered to include triethylbenzene and higher boiling point components in about the 185° C. and above range. This can be seen from an examination of FIG. 7. The heavies content at the lower space velocity of 35 hr.$^{-1}$ was reduced from a value of 0.25 wt. % relative to ethylbenzene for the Catalyst A (curve 7A1) to a value of about 0.15 wt. % relative to ethylbenzene for the higher silica/aluminum ratio Catalyst B (curve 7B1). In terms of product concentration, and assuming an ethylbenzene content of about 12% in the reactor effluent, this indicates that operating in accordance with the present invention can substantially reduce the heavies content of the reactor effluent to a value of about 0.02 wt. % or less. When the space velocity is increased to 70 hr.$^{-1}$, an even further reduction, down to the level of about 0.01 wt. % or below, can be be achieved.

Figure 8:
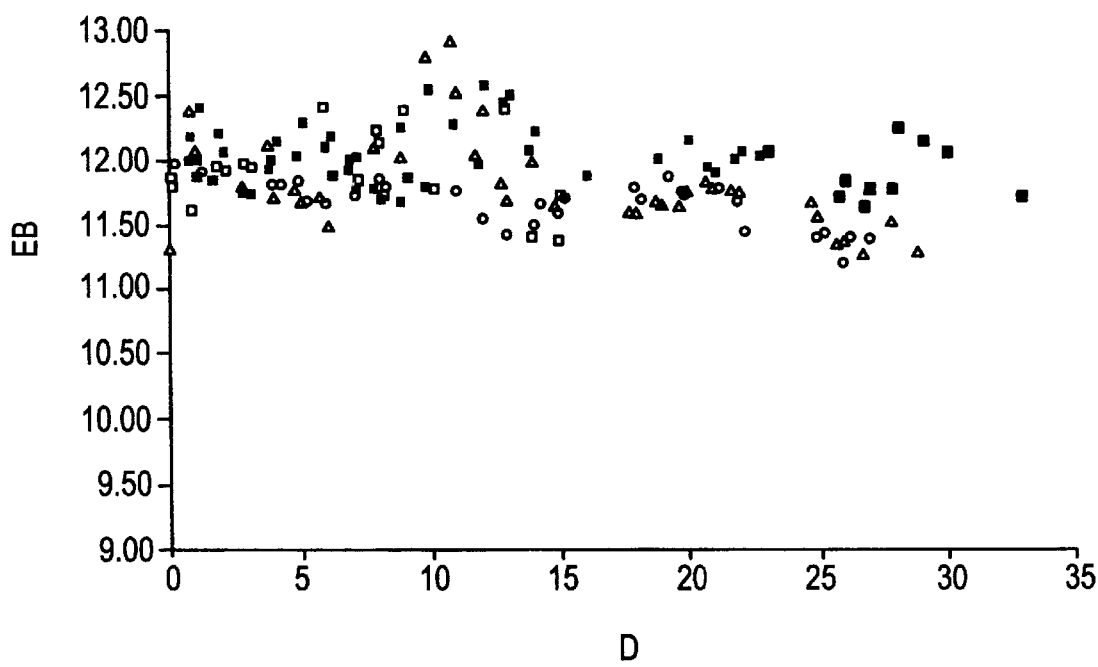
FIG. 8 is an illustration of data points illustrating the effect of space velocity on ethylbenzene production plotted as function of time for the various catalysts at different space velocities.

FIG. 8 shows the weight percent of ethylbenzene (EB) in the reactor effluent as a function of catalyst age for Catalysts A and B at space velocities of 35 and 70 hr.$^{-1}$. Given the scatter of the data and the overlapping data points for the various catalysts at the various space velocities, no curves are presented in FIG. 8. However, it can be seen from the examination of the data presented in FIG. 8 that there was no appreciable difference in the ethylbenzene yields for the catalysts at either the lower or higher space velocity.

As can be seen from the foregoing experimental work, use of the higher silica/alumina ratio catalyst consistently lowers the xylene and heavies content from that associated with use of the comparable Catalyst A of a lower silica/alumina ratio. This is true for both the lower and higher space velocities, thus the higher silica/alumina ratio Catalyst B is particularly well-suited for the operation of a system employing parallel reactors and separate alkylation and transalkylation reactors as described above with reference to FIG. 2. When operating the alkylation reactors in a parallel mode (during normal operations without regeneration), the xylene yield relative to ethylbenzene can be maintained relatively low at a value of about 600 ppm xylene or lower. This contrasts with 900 or more ppm xylene using the lower silica/alumina ratio Catalyst A. When operating a transalkylation reactor at a higher space velocity, as will be involved during a regeneration stage of one of the parallel reactors, the higher silica/alumina ratio Catalyst B results in yet a further dramatic reduction in the xylene yield. While this is accompanied by a significant increase in diethylbenzene yield, as shown in FIG. 4, this can readily be accommodated by the use of the separate transalkylation zone. This is particularly so given that the effect is relatively transitory since the operation of a reactor in the regeneration mode will usually occupy no more than about 5 to 10 percent of the time during which the reactor is operated in the direct alkylation mode. Moreover, the substantially-reduced xylene yield for the silica/alumina Catalyst B is observed at the higher space velocities associated with operation of one of the alkylation reactors in a regeneration mode.

Having described specific embodiments of the present invention, it will be understood that modifications thereof may be suggested to those skilled in the art, and it is intended to cover all such modifications as fall within the scope of the appended claims.

What is claimed:

1. In a process for the production of ethylbenzene and the separate transalkylation of polyethylbenzene, the steps comprising:

a) providing a multistage alkylation reaction zone having a plurality of series connected catalyst beds each containing a pentasil molecular sieve aromatic alkylation catalyst comprising predominantly monoclinic silicalite having a silica/alumina ratio of at least 275;

b) supplying a feedstock containing benzene and ethylene to said alkylation reaction zone;

c) operating said alkylation reaction zone at temperature and pressure conditions in which benzene is in the gaseous phase to cause gas-phase ethylation of said benzene in the presence of said silicalite catalyst to produce an alkylation product comprising a mixture of ethylbenzene and polyalkylated aromatic components including xylene and diethylbenzene;

d) supplying said feedstock to said reaction zone at a flow rate to provide a space velocity of benzene in said feedstock to produce a concentration of xylene in said product which is no more than about 600 ppm based upon ethylbenzene in the product and polyalkylated aromatic components heavier than diethylbenzene of no more than 0.25 wt. % based upon ethylbenzene in the product;

e) recovering said alkylation product from said reaction zone and supplying said product from said reaction zone to an intermediate recovery zone for the separation and recovery of ethylbenzene from the alkylation product and the separation and recovery of a polyalkylated aromatic component including diethylbenzene;

f) supplying at least a portion of said polyalkylated aromatic component including diethylbenzene in said polyalkylated component to a transalkylation reaction zone;

g) supplying benzene to said transalkylation reaction zone; and h) operating said transalkylation reaction zone under temperature and pressure conditions to cause disproportionation of said polyalkylated aromatic fraction to produce a disproportionation product having a reduced diethylbenzene content and an enhanced ethylbenzene content.

2. The process of claim 1 wherein said silicalite catalyst has a silica/alumina ratio of at least 300.

3. The process of claim 1 wherein said silicalite alkylation catalyst has a silica/alumina ratio within the range of 300–350.

4. The process of claim 1 wherein the concentration of xylene in said alkylation product is less than 500 ppm based upon the amount of ethylbenzene in the product.

5. The method of claim 1 wherein said reaction product has an ortho-xylene content less than the thermodynamic equilibrium content of ortho-xylene at the temperature and pressure of said reaction zone.

6. The method of claim 1 wherein the orthoxylene content of said reaction product is no more than about 10 wt. % of the total xylene content in said reaction product.

17

7. The method of claim 1, wherein said alkylation catalyst comprises predominantly monoclinic silicalite having a crystal size of 0.5µ or less and formulated with an alumina binder to provide catalyst particles having a surface area/volume ratio of at least 60 in.$^{-1}$.

8. The method of claim 1, wherein said alkylation catalyst comprises predominantly monoclinic silicalite having a crystal size of less than one micron.

9. The process of claim 1 wherein said transalkylation reaction zone contains a zeolite Y transalkylation catalyst and is operated under temperature and pressure conditions effective to maintain the feedstock in said transalkylation zone in the liquid phase.

10. The process of claim 1 wherein said feedstock is intermittently supplied to said alkylation zone at an enhanced flow rate providing a designated benzene space velocity producing a diethylbenzene content which is sufficiently greater than the diethylbenzene content produced at a benzene space velocity of one-half of said designated space velocity to provide a ratio of the diethylbenzene content at said designated benzene space velocity to the diethylbenzene content at a benzene space velocity of one-half of said designated space velocity of about 1.2 or more.

11. In a process for the production of ethylbenzene and the separate transalkylation of polyethylbenzene, the steps comprising:

a) providing a multi-stage alkylation reaction zone having a plurality of series connected catalyst beds each containing a pentasil molecular sieve aromatic alkylation catalyst comprising predominantly monoclinic silicalite having a silica/alumina ratio of at least 275;

b) supplying a feedstock containing benzene and ethylene to said alkylation reaction zone;

c) operating said alkylation reaction zone at temperature and pressure conditions in which benzene is in the gaseous phase to cause gas-phase ethylation of said benzene in the presence of said silicalite catalyst to produce an alkylation product comprising a mixture of ethylbenzene and polyalkylated aromatic components including xylene and diethylbenzene;

d) supplying said feedstock to said reaction zone at a flow rate to provide a space velocity of benzene in said feedstock to produce a concentration of xylene in said product which is no more than about 600 ppm based upon ethylbenzene in the product and polyalkylated aromatic components heavier than diethylbenzene of no more than 0.25 wt. % based upon ethylbenzene in the product;

e) recovering said alkylation product from said reaction zone and supplying said product from said reaction zone to an intermediate recovery zone for the separation and recovery of ethylbenzene from the alkylation product and the separation and recovery of a polyalkylated aromatic component including diethylbenzene;

f) supplying at least a portion of said polyalkylated aromatic component including diethylbenzene in said polyalkylated component to a transalkylation reaction zone containing a zeolite transalkylation catalyst comprising a molecular sieve having a pore size greater than the pore size of said silicalite alkylation catalyst;

g) supplying benzene to said transalkylation reaction zone; and h) operating said transalkylation reaction zone under temperature and pressure conditions to maintain benzene in the liquid phase and effective to cause disproportionation of said polyalkylated aromatic fraction to produce a disproportionation product having a reduced diethylbenzene content and an enhanced ethylbenzene content.

12. The process of claim 11 wherein said silicalite alkylation catalyst has a silica/alumina ratio within the range of 300–350.

13. The method of claim 12 wherein the orthoxylene content of said reaction product is less than the thermodynamic equilibrium content of orthoxylene at the temperature and pressure of said reaction zone.

14. The process of claim 11 wherein said transalkylation reaction zone contains a zeolite Y transalkylation catalyst and is operated under temperature and pressure conditions effective to maintain the feedstock in said transalkylation zone in the liquid phase.

15. In a process for the production of ethylbenzene and the separate transalkylation of polyethylbenzene, the steps comprising:

a) providing a first multi-stage alkylation reaction zone having a plurality of series connected catalyst beds each containing a pentasil molecular sieve aromatic alkylation catalyst comprising predominantly monoclinic silicalite having a silica/alumina ratio of at least 275;

b) providing at least a second multi-stage alkylation reaction zone having a plurality of series connected catalyst beds each containing a pentasil molecular sieve aromatic alkylation catalyst comprising predominantly monoclinic silicalite having a silica/alumina ratio of at least 275;

c) supplying a feedstock containing benzene and ethylene to said first and second alkylation reaction zones;

d) operating said alkylation reaction zones in a paralleled mode at temperature and pressure conditions in which benzene is in the gaseous phase to cause gas-phase ethylation of said benzene in the presence of said silicate catalyst to produce an alkylation product comprising a mixture of ethylbenzene and polyalkylated aromatic components including xylene and diethylbenzene;

e) supplying said feedstock to said reaction zones at a flow rate to provide in each of said reaction zones a space velocity of benzene in said feedstock to produce a concentration of xylene in said product which is about 600 ppm or less based upon ethylbenzene in the product;

f) recovering said alkylation product from said reaction zones and supplying said product from said reaction zones to an intermediate recovery zone for the separation and recovery of ethylbenzene from the alkylation product and the separation and recovery of a polyalkylated aromatic component including diethylbenzene;

g) supplying at least a portion of said polyalkylated aromatic component including diethylbenzene in said polyalkylated component to a transalkylation reaction zone;

h) supplying benzene to said transalkylation reaction zone;

i) operating said transalkylation reaction zone under temperature and pressure conditions to cause disproportionation of said polyalkylated aromatic fraction to produce a disproportionation product having a reduced diethylbenzene content and an enhanced ethylbenzene content; and j) terminating the supply of said feedstock to said second reaction zone and concomitantly therewith supplying said feedstock to said first reaction zone at a flow rate to provide in said first reaction zone an enhanced space velocity of benzene in said feedstock which is greater than the space velocity associated with a minimum concentration of diethylbenzene in said reaction product, said space velocity providing a diethylbenzene content which is greater than said minimum concentration of diethylbenzene and an attendant concentration of xylene in said product which is less than 600 ppm based upon ethylbenzene in said product.

16. The process of claim 15 further comprising the step subsequent to step (j) placing said second reaction zone back on stream and re-establishing the supply of said feedstock to said second reaction zone and thereafter terminating the supply of said feedstock to said first reaction zone and concomitantly therewith supplying said feedstock to said second reaction zone at a flow rate to provide in said second reaction zone an enhanced space velocity of benzene in said feedstock which is greater than the space velocity associated with a minimum concentration of diethylbenzene in said reaction product, said space velocity providing a diethylbenzene content which is greater than said minimum concentration of diethylbenzene and an attendant concentration of xylene in said product which is about 600 ppm or less based upon ethylbenzene in said product.

17. The process of claim 15 wherein said transalkylation reaction zone contains a zeolite transalkylation catalyst comprising a molecular sieve having a pore size greater than the pore size of said silicalite catalyst.

18. The process of claim 15 wherein said feedstock is supplied to said first alkylation reaction zone at an enhanced benzene space velocity in step (j) producing a diethylbenzene content which is sufficiently greater than the diethylbenzene content produced at a benzene space velocity of one-half of said enhanced space velocity to provide a ratio of the diethylbenzene content at said designated benzene space velocity to the diethylbenzene content at a benzene space velocity of one-half of said enhanced space velocity of about 1.2 or more.

19. The process of claim 15 wherein said transalkylation reaction zone contains a zeolite Y transalkylation catalyst and is operated under temperature and pressure conditions effective to maintain the feedstock in said transalkylation zone in the liquid phase.

20. The method of claim 15, wherein said alkylation catalyst comprises predominantly monoclinic silicalite having a crystal size of less than one micron.

21. The method of claim 15 wherein the orthoxylene content of said reaction product is less than the thermodynamic equilibrium content of orthoxylene at the temperature and pressure of said reaction zone.

* * * * *